(12) United States Patent
Urano et al.

(10) Patent No.: US 12,269,874 B2
(45) Date of Patent: Apr. 8, 2025

(54) ANTIBODY THAT RECOGNIZES NEOEPITOPE OF ACTIVATED INTERLEUKIN-18 PROTEINS AND APPLICATION THEREOF

(71) Applicant: mAbProtein Co., Ltd., Izumo (JP)

(72) Inventors: Takeshi Urano, Izumo (JP); Yuko Nariai, Izumo (JP); Hiroki Kamino, Izumo (JP); Eiji Obayashi, Izumo (JP)

(73) Assignee: mAbProtein Co., Ltd., Shimane (JP)

( * ) Notice: Subject to any disclaimer, the term of this patent is extended or adjusted under 35 U.S.C. 154(b) by 1037 days.

(21) Appl. No.: 17/264,479

(22) PCT Filed: Dec. 3, 2019

(86) PCT No.: PCT/JP2019/047154
§ 371 (c)(1),
(2) Date: Jan. 29, 2021

(87) PCT Pub. No.: WO2020/116423
PCT Pub. Date: Jun. 11, 2020

(65) Prior Publication Data
US 2021/0317200 A1   Oct. 14, 2021

(30) Foreign Application Priority Data

Dec. 3, 2018 (JP) ................................. 2018-226667
Jun. 4, 2019 (JP) ................................. 2019-104826

(51) Int. Cl.
*C07K 16/24* (2006.01)
*G01N 33/53* (2006.01)

(52) U.S. Cl.
CPC ........... *C07K 16/244* (2013.01); *G01N 33/53* (2013.01); *C07K 2317/32* (2013.01); *C07K 2317/565* (2013.01); *G01N 2333/54* (2013.01)

(58) Field of Classification Search
CPC .............. C07K 16/244; C07K 2317/32; C07K 2317/565; G01N 33/53; G01N 2333/54
See application file for complete search history.

(56) References Cited

U.S. PATENT DOCUMENTS

| 6,197,297 B1 | 3/2001 | Kunikata et al. |
| 10,570,199 B2 | 2/2020 | Shimizu et al. |
| 2017/0355756 A1* | 12/2017 | Julien ................. C07K 16/18 |

FOREIGN PATENT DOCUMENTS

| JP | 8-231598 | 9/1996 |
| JP | 2012-139223 | 7/2012 |

(Continued)

OTHER PUBLICATIONS

Chen et al., Enhancement and destruction of antibody function by somatic mutation: unequal occurrence is controlled by V gene combinatorial associations. EMBO J. Jun. 15, 1995;14(12):2784-94. (Year: 1995).*

(Continued)

*Primary Examiner* — Aurora M Fontainhas
*Assistant Examiner* — Selam Berhane
(74) *Attorney, Agent, or Firm* — Rankin, Hill & Clark LLP

(57) ABSTRACT

Antibodies 9-10.2 and 8-4.1 that recognize YFGKLESK, which is 8 amino acids present in a neoepitope formed as a result of a precursor pro-IL-18 being cleaved by caspase-1 or caspase-4 are prepared. Accordingly, an antibody that recognizes only activated IL-18 can be provided.

10 Claims, 12 Drawing Sheets
Specification includes a Sequence Listing.

(56) References Cited

FOREIGN PATENT DOCUMENTS

| | | | |
|---|---|---|---|
| JP | 2012-139224 | 7/2012 | |
| JP | WO2012/124683 | 7/2014 | |
| JP | WO2014/080866 | 1/2017 | |
| WO | 01/058956 | 8/2001 | |
| WO | 2005/047307 | 5/2005 | |
| WO | WO-2008068048 A2 * | 6/2008 | ............ A61P 31/10 |
| WO | 2010/020593 | 2/2010 | |
| WO | 2010/048183 | 4/2010 | |
| WO | 2011/098424 | 8/2011 | |
| WO | 2012/085015 | 6/2012 | |
| WO | 2014/037899 | 3/2014 | |
| WO | 2015/032932 | 3/2015 | |
| WO | 2016/139297 | 9/2016 | |

OTHER PUBLICATIONS

Edwards et al., The remarkable flexibility of the human antibody repertoire; isolation of over one thousand different antibodies to a single protein, BLyS. J Mol Biol. Nov. 14, 2003;334(1): 103-18. (Year: 2003).*

Koenig et al., Mutational landscape of antibody variable domains reveals a switch modulating the interdomain conformational dynamics and antigen binding. PNAS Jan. 24, 2017 114 (4) E486-E495; first published Jan. 5, 2017; (Year: 2017).*

Kussie, Paul H., "A Single Engineered Amino Acid Substitution Changes Antibody Fine Specificity", 1994, Journal of Immunology 152(1): pp. 146-152. (Year: 1994).*

Arend et al., "IL-1, IL-18, and IL-33 familes of cytokines", Immunological Reviews, 2008, vol. 223, pp. 20-38, Singapore; discussed in the specification.

Sanders et al., "Role of Interleukin-18 in the Pathophysiology of Allergic Diseases", Cytokine Growth Factor Rev., 2016, vol. 32, pp. 31-39, New Orleans, LA; discussed in the specification.

Hirel et al., "Extent of N-terminal methionine excision from *Escherichia coli* proteins is governed by the side-chain ength of the penultimate amino acid", Proc. Natl. Acad. Sci. USA, Nov. 1989, vol. 86, pp. 8247-8251, France; discussed in the specification.

Dalboge et al., "In vivo processing of N-terminal methionine in *E. coli*", FEBS, Jun. 1990, vol. 266, No. 1,2, pp. 1-3, Denmark; discussed in the specification.

Girard et al., "Elevated serum levels of free interleukin-18 in adult-onset Still's disease", Rheumatology, 2016, vol. 55, pp. 2237-2247, Switzerland; discussed in the specification.

Okamura et al., "Cloning of a new cytokine that induces IFN-γ production by T cells", Nature, Nov. 1995, vol. 378, pp. 88-91, Japan; discussed in the specification.

Krumm et al., "Structural basis for antagonism of human interleukin 18 by poxvirus interleukin 18-binding protein", PNAS, Dec. 30, 2008, vol. 105, No. 52, pp. 20711-20715, Texas; discussed in the specification.

Krumm et al., A Unique Bivalent Binding and Inhibition Mechanism by the Yatapoxvirus Interleukin 18 Binding Protein, PLOS Pathogens, Aug. 2012, vol. 8, Issue 8, e1002876, pp. 1-15, Texas; discussed in the specification.

Furuya et al., "An immuno-polymerase chain reaction assay for human interleukin-18", Journal of Immunological Methods, 2000, vol. 238, pp. 173-180.

Moriwaki et al., "Elevated Levels of Interleukin-18 and Tumor Necrosis Factor-α in Serum of Patients With Type 2 Diabetes Mellitus: Relationship With Diabetic Nephropathy", Metabolism, May 2003, vol. 52, No. 5, pp. 605-608.

* cited by examiner

SEQUENCE LISTING

<160> NUMBER OF SEQ ID NOS: 42

<210> SEQ ID NO 1
<211> LENGTH: 9
<212> TYPE: PRT
<213> ORGANISM: Artificial Sequence
<220> FEATURE:
<223> OTHER INFORMATION: synthetic peptide

<400> SEQUENCE: 1

Tyr Phe Gly Lys Leu Glu Ser Lys Cys
1               5

<210> SEQ ID NO 2
<211> LENGTH: 6
<212> TYPE: PRT
<213> ORGANISM: Artificial Sequence
<220> FEATURE:
<223> OTHER INFORMATION: epitope of hybridoma 11-4.1

<400> SEQUENCE: 2

Arg Pro Leu Phe Glu Asp
1               5

<210> SEQ ID NO 3
<211> LENGTH: 5
<212> TYPE: PRT
<213> ORGANISM: Artificial Sequence
<220> FEATURE:
<223> OTHER INFORMATION: synthetic peptide

<400> SEQUENCE: 3

Asp Leu Val Pro Arg
1               5

<210> SEQ ID NO 4
<211> LENGTH: 8
<212> TYPE: PRT
<213> ORGANISM: Homo sapiens

<400> SEQUENCE: 4

Tyr Phe Gly Lys Leu Glu Ser Lys
1               5

<210> SEQ ID NO 5
<211> LENGTH: 4
<212> TYPE: PRT
<213> ORGANISM: Homo sapiens

<400> SEQUENCE: 5

Tyr Phe Gly Lys
1

<210> SEQ ID NO 6
<211> LENGTH: 30
<212> TYPE: DNA
<213> ORGANISM: Artificial Sequence
<220> FEATURE:
<223> OTHER INFORMATION: sequence primer

<400> SEQUENCE: 6
ggggatccag gtsmarctgc agsagtcwgg                                   30

<210> SEQ ID NO 7
<211> LENGTH: 31
<212> TYPE: DNA

```
<213> ORGANISM: Artificial Sequence
<220> FEATURE:
<223> OTHER INFORMATION: sequence primer

<400> SEQUENCE: 7
gggaattcct tgaccaggca tcctagagtc a                                    31

<210> SEQ ID NO 8
<211> LENGTH: 32
<212> TYPE: DNA
<213> ORGANISM: Artificial Sequence
<220> FEATURE:
<223> OTHER INFORMATION: sequence primer

<400> SEQUENCE: 8
ggggatccga yattgtgmts acmcarwctm ca                                   32

<210> SEQ ID NO 9
<211> LENGTH: 29
<212> TYPE: DNA
<213> ORGANISM: Artificial Sequence
<220> FEATURE:
<223> OTHER INFORMATION: sequence primer

<400> SEQUENCE: 9
gggaattcga agatggatac agttggtgc                                       29

<210> SEQ ID NO 10
<211> LENGTH: 315
<212> TYPE: DNA
<213> ORGANISM: Mus musculus

<400> SEQUENCE: 10
agtctgactt gttctttctc tgggttttca ctgagcagtt ctggtatggg tgtaggctgg     60
attcgtcagc cttcagggaa gggtctggag tggctggcac acatttggtg ggatgatgat    120
aagaattata acccaggcct gaagagtcgg ctcacaatct ccaaggatac ttccaaaaac    180
caggtattcc tcaagatcgc caatgtggac actgcagatg ctgccacata ctactgtact    240
cgaacgagga cgtatagtaa cttcggaggt ggtatggcct actggggtac aaggaacctc    300
agtcaccgtc tcctc                                                    315

<210> SEQ ID NO 11
<211> LENGTH: 105
<212> TYPE: PRT
<213> ORGANISM: Mus musculus

<400> SEQUENCE: 11

Ser Leu Thr Cys Ser Phe Ser Gly Phe Ser Leu Ser Ser Ser Gly Met
1               5                   10                  15

Gly Val Gly Trp Ile Arg Gln Pro Ser Gly Lys Gly Leu Glu Trp Leu
            20                  25                  30

Ala His Ile Trp Trp Asp Asp Asp Lys Asn Tyr Asn Pro Gly Leu Lys
        35                  40                  45

Ser Arg Leu Thr Ile Ser Lys Asp Thr Ser Lys Asn Gln Val Phe Leu
    50                  55                  60

Lys Ile Ala Asn Val Asp Thr Ala Asp Ala Ala Thr Tyr Tyr Cys Thr
65                  70                  75                  80

Arg Thr Arg Thr Tyr Ser Asn Phe Gly Gly Gly Met Ala Tyr Trp Gly
                85                  90                  95

Thr Arg Asn Leu Ser His Arg Leu Leu
```

<210> SEQ ID NO 12
<211> LENGTH: 301
<212> TYPE: DNA
<213> ORGANISM: Mus musculus

<400> SEQUENCE: 12

```
ctgtccatca cttgcactgt ctctgggttt tcattaacca gctatggtgt acactgggtt    60
cgccagcctc caggaaaggg tctggagtgg ctggagtaa tatgggctgg tggaagcaca   120
aattataatt cggctctcat gtccagactg agcatcagca agacaactc caagagccaa   180
gttttcttaa aaatgaacag tctgcaaact gatgacacag ccatgtacta ctgtgccaga   240
gaaagtagct acgatgctat ggactactgg ggtcaaggaa cctcagtcac cgtctcctca   300
g                                                                  301
```

<210> SEQ ID NO 13
<211> LENGTH: 100
<212> TYPE: PRT
<213> ORGANISM: Mus musculus

<400> SEQUENCE: 13

```
Leu Ser Ile Thr Cys Thr Val Ser Gly Phe Ser Leu Thr Ser Tyr Gly
1               5                   10                  15
Val His Trp Val Arg Gln Pro Pro Gly Lys Gly Leu Glu Trp Leu Gly
            20                  25                  30
Val Ile Trp Ala Gly Gly Ser Thr Asn Tyr Asn Ser Ala Leu Met Ser
        35                  40                  45
Arg Leu Ser Ile Ser Lys Asp Asn Ser Lys Ser Gln Val Phe Leu Lys
    50                  55                  60
Met Asn Ser Leu Gln Thr Asp Asp Thr Ala Met Tyr Tyr Cys Ala Arg
65                  70                  75                  80
Glu Ser Ser Tyr Asp Ala Met Asp Tyr Trp Gly Gln Gly Thr Ser Val
                85                  90                  95
Thr Val Ser Ser
            100
```

<210> SEQ ID NO 14
<211> LENGTH: 288
<212> TYPE: DNA
<213> ORGANISM: Mus musculus

<400> SEQUENCE: 14

```
cttggagatc aagcctccat ctcttgcaga tctagtcaga gcattgcaca tagtaatgga    60
tacacctatt tagaatggta cctgcagaca ccaggccagt ctccaaagct cctgatctac   120
aaagttttcc aacagatttc tggggtccca gacaggttca gtggcagtgg atcagggaca   180
gatttcacac tcaagatcag cagagtggag gctgaggatc tgggagttta ttactgcgtt   240
caaggttcac atgttccgct cacgttcggg gctgggacca agctggag               288
```

<210> SEQ ID NO 15
<211> LENGTH: 98
<212> TYPE: PRT
<213> ORGANISM: Mus musculus

<400> SEQUENCE: 15

```
Leu Gly Asp Gln Ala Ser Ile Ser Cys Arg Ser Ser Gln Ser Ile Ala
1               5                   10                  15
```

```
His Ser Asn Gly Tyr Thr Tyr Leu Glu Trp Tyr Leu Gln Thr Pro Gly
            20                  25                  30

Gln Ser Pro Lys Leu Leu Ile Tyr Lys Val Ser Asn Arg Phe Ser Gly
        35                  40                  45

Val Pro Asp Arg Phe Ser Gly Ser Gly Thr Asp Phe Thr Leu
50                  55                  60

Lys Ile Ser Arg Val Glu Ala Glu Asp Leu Gly Val Tyr Tyr Cys Val
65                  70                  75                  80

Gln Gly Ser His Val Pro Leu Thr Phe Gly Ala Gly Thr Lys Leu Glu
                85                  90                  95

Leu Lys

<210> SEQ ID NO 16
<211> LENGTH: 321
<212> TYPE: DNA
<213> ORGANISM: Mus musculus

<400> SEQUENCE: 16
gatattgtga tcacacaatc tcccaaatcc atgtccatgt cagtaggaga gagggtcacc      60
ttgacctgca aggccagtga aatgtggtt acttatgttt cctggtatca acagaaacca     120
gagcagtctc ctaaactgat gatatacggg gcatccaacc ggtacactgg ggtccccgat     180
cgcttcacag gcagtggatc tgcaacagat ttcactctga ccatcagcag tgtgcaggct     240
gaagaccttg cagattatca ctgtggacag ggttacagct atccgtacac gttcggaggg     300
gggaccaagc tggaaataaa a                                               321

<210> SEQ ID NO 17
<211> LENGTH: 107
<212> TYPE: PRT
<213> ORGANISM: Mus musculus

<400> SEQUENCE: 17

Asp Ile Val Ile Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Met Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys
                100                 105

<210> SEQ ID NO 18
<211> LENGTH: 30
<212> TYPE: DNA
<213> ORGANISM: Mus musculus

<400> SEQUENCE: 18
gggttttcac tgagcagttc tggtatgggt                                       30

<210> SEQ ID NO 19
```

```
<211> LENGTH: 21
<212> TYPE: DNA
<213> ORGANISM: Mus musculus

<400> SEQUENCE: 19
atttggtggg atgatgataa g                                      21

<210> SEQ ID NO 20
<211> LENGTH: 45
<212> TYPE: DNA
<213> ORGANISM: Mus musculus

<400> SEQUENCE: 20
actcgaacga ggacgtatag taacttcgga ggtggtatgg cctac            45

<210> SEQ ID NO 21
<211> LENGTH: 33
<212> TYPE: DNA
<213> ORGANISM: Mus musculus

<400> SEQUENCE: 21
cagagcattg cacatagtaa tggatacacc tat                         33

<210> SEQ ID NO 22
<211> LENGTH: 9
<212> TYPE: DNA
<213> ORGANISM: Mus musculus

<400> SEQUENCE: 22 aaagtttcc                                                     9

<210> SEQ ID NO 23
<211> LENGTH: 27
<212> TYPE: DNA
<213> ORGANISM: Mus musculus

<400> SEQUENCE: 23
gttcaaggtt cacatgttcc gctcacg                                27

<210> SEQ ID NO 24
<211> LENGTH: 10
<212> TYPE: PRT
<213> ORGANISM: Mus musculus

<400> SEQUENCE: 24

Gly Phe Ser Leu Ser Ser Ser Gly Met Gly
1               5                   10

<210> SEQ ID NO 25
<211> LENGTH: 7
<212> TYPE: PRT
<213> ORGANISM: Mus musculus

<400> SEQUENCE: 25

Ile Trp Trp Asp Asp Asp Lys
1               5

<210> SEQ ID NO 26
<211> LENGTH: 15
<212> TYPE: PRT
<213> ORGANISM: Mus musculus

<400> SEQUENCE: 26

Thr Arg Thr Arg Thr Tyr Ser Asn Phe Gly Gly Gly Met Ala Tyr
```

-continued

<210> SEQ ID NO 27
<211> LENGTH: 11
<212> TYPE: PRT
<213> ORGANISM: Mus musculus

<400> SEQUENCE: 27

Gln Ser Ile Ala His Ser Asn Gly Tyr Thr Tyr
1               5                   10

<210> SEQ ID NO 28
<211> LENGTH: 3
<212> TYPE: PRT
<213> ORGANISM: Mus musculus

<400> SEQUENCE: 28

Lys Val Ser
1

<210> SEQ ID NO 29
<211> LENGTH: 9
<212> TYPE: PRT
<213> ORGANISM: Mus musculus

<400> SEQUENCE: 29

Val Gln Gly Ser His Val Pro Leu Thr
1               5

<210> SEQ ID NO 30
<211> LENGTH: 24
<212> TYPE: DNA
<213> ORGANISM: Mus musculus

<400> SEQUENCE: 30
gggttttcat taaccagcta tggt                                          24

<210> SEQ ID NO 31
<211> LENGTH: 21
<212> TYPE: DNA
<213> ORGANISM: Mus musculus

<400> SEQUENCE: 31
atatgggctg gtggaagcac a                                             21

<210> SEQ ID NO 32
<211> LENGTH: 33
<212> TYPE: DNA
<213> ORGANISM: Mus musculus

<400> SEQUENCE: 32
gccagagaaa gtagctacga tgctatggac tac                                33

<210> SEQ ID NO 33
<211> LENGTH: 18
<212> TYPE: DNA
<213> ORGANISM: Mus musculus

<400> SEQUENCE: 33
gagaatgtgg ttacttat                                                 18

<210> SEQ ID NO 34
<211> LENGTH: 9
<212> TYPE: DNA

<213> ORGANISM: Mus musculus

<400> SEQUENCE: 34 ggggcatcc                                                                                          9

<210> SEQ ID NO 35
<211> LENGTH: 27
<212> TYPE: DNA
<213> ORGANISM: Mus musculus

<400> SEQUENCE: 35
ggacagggtt acagctatcc gtacacg                                                                     27

<210> SEQ ID NO 36
<211> LENGTH: 8
<212> TYPE: PRT
<213> ORGANISM: Mus musculus

<400> SEQUENCE: 36

Gly Phe Ser Leu Thr Ser Tyr Gly
1               5

<210> SEQ ID NO 37
<211> LENGTH: 7
<212> TYPE: PRT
<213> ORGANISM: Mus musculus

<400> SEQUENCE: 37

Ile Trp Ala Gly Gly Ser Thr
1               5

<210> SEQ ID NO 38
<211> LENGTH: 11
<212> TYPE: PRT
<213> ORGANISM: Mus musculus

<400> SEQUENCE: 38

Ala Arg Glu Ser Ser Tyr Asp Ala Met Asp Tyr
1               5                   10

<210> SEQ ID NO 39
<211> LENGTH: 6
<212> TYPE: PRT
<213> ORGANISM: Mus musculus

<400> SEQUENCE: 39

Glu Asn Val Val Thr Tyr
1               5

<210> SEQ ID NO 40
<211> LENGTH: 3
<212> TYPE: PRT
<213> ORGANISM: Mus musculus

<400> SEQUENCE: 40

Gly Ala Ser
1

<210> SEQ ID NO 41
<211> LENGTH: 9
<212> TYPE: PRT
<213> ORGANISM: Mus musculus

<400> SEQUENCE: 41

```
Gly Gln Gly Tyr Ser Tyr Pro Tyr Thr
1               5

<210> SEQ ID NO 42
<211> LENGTH: 5
<212> TYPE: PRT
<213> ORGANISM: Homo Sapiens

<400> SEQUENCE: 42

Tyr Phe Gly Lys Leu
1               5
```

ANTIBODY THAT RECOGNIZES NEOEPITOPE OF ACTIVATED INTERLEUKIN-18 PROTEINS AND APPLICATION THEREOF

TECHNICAL FIELD

The present invention relates to an antibody that recognizes only activated interleukin-18 (hereinafter referred to as IL-18) protein that is an inflammatory cytokine, and an application thereof.

BACKGROUND ART

IL-18 is a cytokine of the IL-1β family, and is mainly expressed in macrophages, but also expressed in various cells such as dendritic cells, epithelial cells, and keratinocytes. In addition, IL-18 receptors are expressed in various cells such as B cells, neutrophils, macrophages, vascular endothelial cells, and smooth muscle cells, besides NK cells, NKT cells, and CD4$^+$ T cells. The diversity of IL-18-expressing cells and IL-18 receptor-expressing cells indicates the diversity of IL-18 functions, and IL-18 is known to be involved in various immune systems.

IL-18 was shown to play an important role in the defense mechanism against pathogens such as parasites and bacterial infections, when initially discovered, but has also been shown to play an important role in allergic diseases and autoimmune diseases (Non Patent Literatures 1 and 2).

Unlike cytokines such as TNF, IL-18 is not regulated in production at mRNA level and is abundantly present in cells as an inactive precursor (pro-IL-18). The precursor pro-IL-18 is cleaved by caspase-1 or caspase-4 into a peptide at positions 37-193, thereby forming a neoepitope, becoming active, and being released extracellularly. Thus, measuring the amount of mRNA expression or the precursor protein in the cell does not measure the activity of IL-18.

IL-18 is involved in various immune systems, and there are many diseases that are believed to be caused by excessive extracellular release of activated IL-18. Thus, if the measurement of activated IL-18 is achieved, it can be used to diagnose and treat IL-18-related diseases.

Numerous antibodies that specifically recognize IL-18 have been reported (e.g., Patent Literatures 1 to 10). Many of these serve as neutralizing antibodies, and only a few antibodies are disclosed for epitopes. In addition, despite many disclosures for antibodies, there have been no reports of an antibody that recognizes only activated IL-18.

CITATION LIST

Patent Literatures

Patent Literature 1: WO 2016/139297
Patent Literature 2: WO 2015/032932
Patent Literature 3: WO 2014/080866
Patent Literature 4: WO 2012/085015
Patent Literature 5: WO 2014/037899
Patent Literature 6: Japanese Patent Laid-Open No. 2012-139224
Patent Literature 7: Japanese Patent Laid-Open No. 2012-139223
Patent Literature 8: WO 2011/098424
Patent Literature 9: WO 2010/048183
Patent Literature 10: WO 2010/020593
Patent Literature 11: WO 2012/124683

Non Patent Literatures

Non Patent Literature 1: Arend, W. P. et al., Immunol. Rev., 2008, Vol. 223, p. 20-38.
Non Patent Literature 2: Sanders, N. L. & Mishra, A., Cytokine Growth Factor Rev., 2016, Vol. 32, pp. 31-39.
Non Patent Literature 3: Hirel, P-H. et al., Proc. Natl. Acad. Sci. USA, 1989, Vol. 89, pp. 8247-8251.
Non Patent Literature 4: Dalboge, H. et al., FEBS Lett., 1990, Vol. 266(1-2), pp. 1-3.
Non Patent Literature 5: Girard, C. et al., Rheumatology (Oxford), 2016, Vol. 55(12), pp. 2237-2247.
Non Patent Literature 6: Okamura, H. et al., Nature, 1995, Vol. 378(6652), pp. 88-91.
Non Patent Literature 7: Krumm, B. et al., Proc. Natl. Acad. Sci. USA, 2008, Vol. 105, pp. 20711-20715.
Non Patent Literature 8: Krumm, B. et al., PLOS Pathogens, 2012, Vol. 8, Issue 8, e1002876.

SUMMARY OF INVENTION

Technical Problem

Several groups, including the group of the present inventors, have attempted to produce an antibody that recognizes only activated IL-18. However, to date, no antibody that recognizes activated IL-18 has been produced.

The present inventors attempted to produce an antibody that recognizes only activated IL-18, by cleaving pro-IL-18 by caspase ¼, then immunizing with activated IL-18. However, while six monoclonal antibodies that recognize positions 62-70 of IL-18 and two antibodies that recognize the region at positions 128-142 were obtained, they recognize both activated IL-18 and pro-IL-18, and no antibody that recognizes only activated IL-18 was obtained.

Most antibodies disclosed in Patent Literatures 1 to 10 are antibodies that exhibit neutralizing activity. For example, antibodies disclosed in Patent Literatures 1 to 4 are antibodies that bind to a binding site of an IL-18 binding protein (IL-18BP) or a vicinity thereof. Patent Literature 5 discloses antibodies that do not bind to IL-18 bound by IL-18BP. Patent Literature 6 discloses antibodies that inhibit IL-18 activity. Although the peptide sequence of the N-terminus (amino acid positions 37 to 50) of activated IL-18 is also disclosed as an epitope, the epitope of the antibody actually obtained is a different region, and it is not disclosed that the antibody recognizes only activated IL-18. Patent Literatures 7 and 8 disclose antibodies having neutralizing activity against IL-18. Patent Literatures 9 and 10 describe antibodies that can be used for treatment. However, none of the antibodies disclosed in these literatures is an antibody that recognizes only activated IL-18.

As mentioned above, since no antibody that detects only activated IL-18 has been obtained, activated IL-18 has been analyzed by confirming the molecular weight by western blot technique. Because western blot technique is time consuming and laborious, examination for the presence of activated IL-18 has not been implemented in clinical sites, even for diseases suspected of involving IL-18.

If an antibody that recognizes only activated IL-18 is obtained, it is possible to measure the amount of activated IL-18 by a simple method such as ELISA and the measurement can be used to diagnose an IL-18-related disease. An object of the present invention is to obtain an antibody that specifically recognizes activated IL-18.

Solution to Problem

The present invention relates to a substance that binds to the neoepitope described below, a polyclonal antibody, a monoclonal antibody, a functional fragment of the antibody, and a kit containing the antibody, and a gene encoding the monoclonal antibody or the functional fragment, an amino acid sequence, a humanized antibody, a human antibody, and a pharmaceutical composition. The present invention also relates to a new method for identifying a range of neoepitope, and a kit for use in the method.

(1) An anti-IL-18 antibody that recognizes only activated IL-18.
(2) The anti-IL-18 antibody according to (1), wherein the antibody recognizes a neoepitope of human IL-18.
(3) The anti-IL-18 antibody according to (1) or (2), wherein the anti-IL-18 antibody is a monoclonal antibody and includes: a heavy chain variable domain containing a CDR1H region consisting of an amino acid sequence of GFSLSSSGMG (SEQ ID NO: 24), a CDR2H region consisting of an amino acid sequence of IWDDDK (SEQ ID NO: 25), and a CDR3H region consisting of an amino acid sequence of TRTR-TYSNFGGGMAY (SEQ ID NO: 26); and a light chain variable domain containing a CDR1L region consisting of an amino acid sequence of QSIAHSNGYTY (SEQ ID NO: 27), a CDR2L region consisting of an amino acid sequence of KVS (SEQ ID NO: 28), and a CDR3L region consisting of an amino acid sequence of VQGSHVPLT (SEQ ID NO: 29).
(4) The anti-IL-18 antibody according to (1) or (2), wherein the anti-IL-18 antibody is a monoclonal antibody and includes: a heavy chain variable domain containing a CDR1H region consisting of an amino acid sequence of GFSLTSYG (SEQ ID NO: 36), a CDR2H region consisting of an amino acid sequence of IWAGGST (SEQ ID NO: 37), and a CDR3H region consisting of an amino acid sequence of ARESSYDAMDY (SEQ ID NO: 38); and a light chain variable domain containing a CDR1L region consisting of an amino acid sequence of ENVVTY (SEQ ID NO: 39), a CDR2L region consisting of an amino acid sequence of GAS (SEQ ID NO: 40), and a CDR3L region consisting of an amino acid sequence of GQGYSYPYT (SEQ ID NO: 41).
(5) The anti-IL-18 antibody according to (3), wherein an amino acid sequence of an H chain variable region is SEQ ID NO: 11 and an amino acid sequence of an L chain variable region is SEQ ID NO: 15.
(6) The anti-IL-18 antibody according to (4), wherein an amino acid sequence of an H chain variable region is SEQ ID NO: 13 and an amino acid sequence of an L chain variable region is SEQ ID NO: 17.
(7) A gene comprising a gene encoding the CDR sequence described in (3) or (4), or the variable region described in (5) or (6), as an open reading frame.
(8) A functional fragment of the anti-IL-18 monoclonal antibody according to any one of (3) to (6).
(9) A kit for detecting and/or quantifying activated IL-18, comprising the anti-IL-18 antibody according to any one of (1) to (6) or the functional fragment of the anti-IL-18 monoclonal antibody according to (8).
(10) An anti-IL-18 monoclonal antibody comprising the CDR sequence described in (3) or (4), or the variable region described in (5) or (6), wherein the monoclonal antibody is a humanized antibody or a human antibody.
(11) A functional fragment of the anti-IL-18 monoclonal antibody according to (10).
(12) A pharmaceutical composition for use in treating an IL-18-related disease, comprising the anti-IL-18 monoclonal antibody according to (10) or the functional fragment according to (11) as an active ingredient.
(13) An antibody, or a fragment consisting of a functional fragment thereof, or a binding substance, which binds to an amino acid represented by SEQ ID NO: 5 (YFGK).
(14) An antibody, or a fragment consisting of a functional fragment thereof, or a binding substance, which binds to an amino acid represented by SEQ ID NO: 4 (YFGKLESK).
(15) A method for analyzing a region of neoepitope recognized by an antibody, comprising: producing a peptide of a length of 5 to 15 amino acids from a cleaved end of neoepitope, substituting amino acid of the peptide with alanine or glycine by sequentially and successively from the N-terminus or C-terminus opposite to the cleaved end of neoepitope in a peptide; and analyzing the region of neoepitope recognized by the antibody by measuring binding of the antibody to the peptides.
(16) A kit used for the method for analyzing a region of neoepitope recognized by an antibody according to (15), comprising a substrate, a reagent for crosslinking a peptide, and a reagent for visualizing binding of the antibody.
(17) A method of treating an IL-18-related disease, comprising administering the monoclonal antibody according to any one of (3) to (6) and (10) or the functional fragment of the monoclonal antibody according to any one of (8) and (11) to a subject.
(18) The method of treating according to (17), wherein the subject has a higher value of activated IL-18 than a healthy person.
(19) The method according to (17) or (18), wherein the IL-18-related disease is any one of adult onset Still's disease, macrophage-activated syndrome/blood cell phagocytosis syndrome, ulcerative colitis, Crohn's disease, interstitial lung disease, bronchial asthma, allergic rhinitis, type 2 diabetes, ischemic nephritis, systemic lupus erythematosus, multiple sclerosis, atopic dermatitis, psoriasis, gout, or rheumatoid arthritis.
(20) A diagnostic method, comprising: examining an amount of activated IL-18 using the monoclonal antibody according to any one of (3) to (6) and (10), the functional fragment of the monoclonal antibody according to any one of (8) and (11), or the kit according to (9); and determining as an IL-18-related disease when the activated IL-18 shows a higher value than that in a healthy individual.

DESCRIPTION OF EMBODIMENTS

Figure 1:
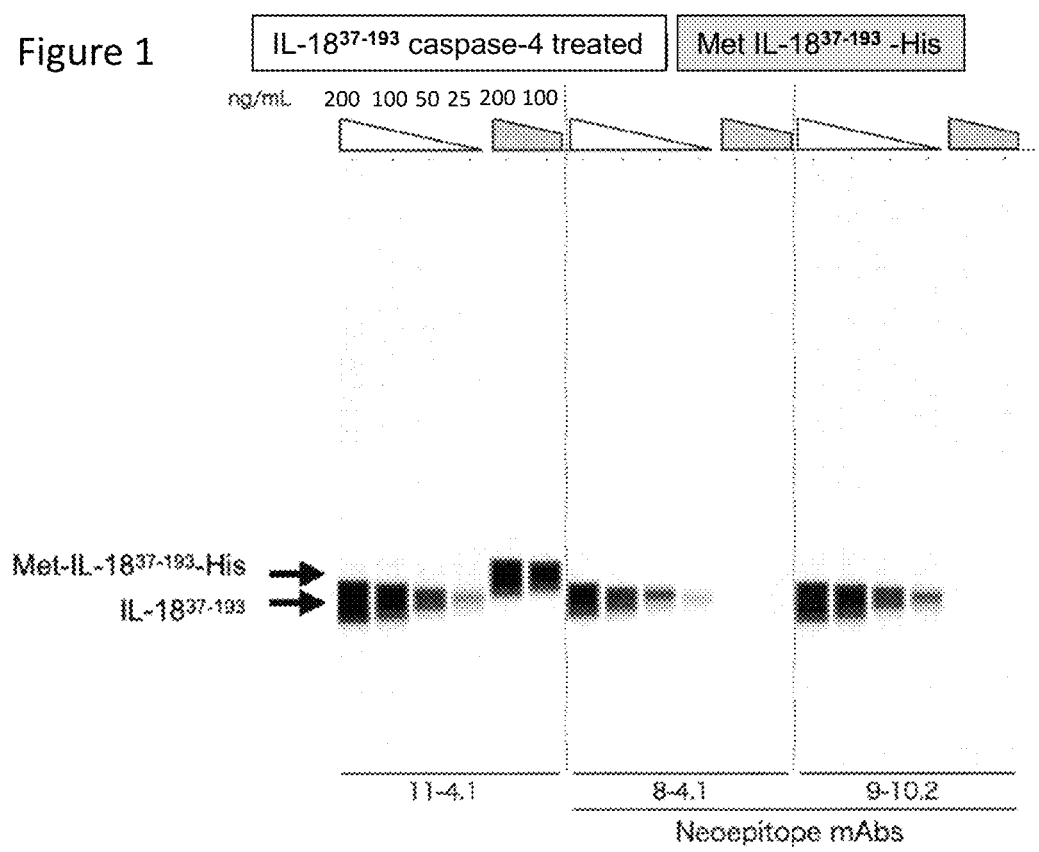
FIG. 1 is a diagram showing analysis by capillary western immunoassay method to confirm that monoclonal antibodies 9-10.2 and 8-4.1 recognize activated IL-18.

The "epitope" refers to a region of an antigen (in the present invention, activated IL-18) recognized by an antibody. The "neoepitope" refers to a protein cleaved end which is newly formed from a protein cleaved by a proteolytic enzyme and is not present in the original protein. In IL-18, pro-IL-18 is cleaved by caspase ¼ to become activated IL-18. A newly formed cleaved end in activated IL-18 is referred to as a neoepitope of IL-18. The "activated IL-18" refers to a peptide at positions 37 to 193 of IL-18 having a neoepitope.

The antibody of the present invention refers to a monoclonal antibody or a derivative that specifically binds to activated IL-18 as shown below. The antibody of the present invention also includes a polyclonal antibody that can be obtained in the same manner as the monoclonal antibody. Furthermore, it includes a functional fragment of the antibody, which exhibits substantially the same antigen specificity as the original antibody. Examples of the functional fragment of the antibody include functional fragments of the antibody such as Fab, Fab', F (ab')$_2$, a single chain antibody (scFv), a disulfide-stabilized V region fragment (dsFv), or a peptide containing CDR.

The antibody of the present invention also include: a humanized antibody such as humanized chimeric antibody and humanized CDR-grafted antibody obtained by using genetic recombination technology, and a human antibody produced by using a genetically modified mouse or a phage display method, from the monoclonal antibody that specifically binds to activated IL-18 identified in the present invention. When administered to a human, a humanized antibody and a human antibody have fewer side effects and exhibit their therapeutic effects longer than antibodies produced by animals other than human.

Furthermore, a substance that binds to the epitope of the cleaved end of activated IL-18 identified in the present invention can also be used for detection of activated IL-18, and the like. Examples of such a substance include a substance other than an antibody, such as a peptide aptamer or a nucleic acid aptamer, which specifically binds to the neoepitope. The aptamer can be produced by a known method such as two-hybrid method or SELEX method.

As used herein, the "IL-18-related disease" refers to a disease caused by excessive extracellular release of activated IL-18 or a disease that may be exacerbated by IL-18. The IL-18-related disease is a disease that is developed and exacerbated by overexpression of IL-18. Examples of the IL-18-related disease include adult onset Still's disease (AOSD), juvenile Still's disease, malignant tumors such as pancreatic cancer, lung cancer and colon cancer, cryopyrin-associated cyclic fever syndrome, systemic lupus erythematosus (SLE), multiple sclerosis, juvenile idiopathic arthritis (JIA), bronchial asthma, bronchiectasis, chronic obstructive pulmonary disease (COPD), transfusion-related lung injury, bronchopulmonary dysplasia (BPD), acute respiratory distress syndrome (ARDS), interstitial pulmonary disease (ILD), idiopathic pulmonary fibrosis, cystic fibrosis, rheumatoid arthritis, metabolic bone disease, severe organ injury in the liver and intestines, heart failure, amyotrophic lateral sclerosis (ALS), dry eye disease (DED), keratitis, corneal angiogenesis, pathological intraocular angiogenesis, iritis, glaucoma, macular degeneration, Sjogren's syndrome, autoimmune uveitis, Behcet's disease, conjunctivitis, allergic conjunctivitis, eyelid dermatitis, allergic rhinitis, type 2 diabetes, non-alcoholic fatty liver disease (NAFLD), steatohepatitis, ischemic reperfusion injury, familial Mediterranean fever, TNF receptor-associated periodic syndrome, high IgD syndrome, gout, Schnitzler's syndrome, microscopic polyangiitis, granulomatous polyangiitis, ANCA-associated vasculitis composed of eosinophilic granulomatous polyangiitis, Hashimoto's disease, Crohn's disease, ulcerative colitis, immunoglobulin-4 (IgG4)-related diseases, pulmonary arterial hypertension, atopic dermatitis, and NLRC4-related autoinflammatory disease (or NLRC4 inflammasome disease).

In these IL-18-related diseases, a therapeutic effect is expected to be obtained by an agent that inhibits the function of IL-18. Accordingly, by examining the expression amount of activated IL-18 in a patient suspected of having an IL-18-related disease, it is possible to determine whether an agent that inhibits a function of IL-18 should be applied to the patient. Furthermore, since the antibody that recognizes neoepitope itself suppresses a function of IL-18 as shown in the Examples below, the antibody that recognizes the neoepitope can be used for treatment.

As used herein, the "kit" refers to a packaged combination of components such as a reagent and an instrument necessary for detecting, quantifying, or evaluating the function of IL-18 using an antibody disclosed in the present description by, but not limited to, western blotting, capillary western immunoassay, immunoprecipitation, immunostaining, or ELISA shown in the Examples below. In addition, the kit for analyzing a neoepitope refers to a packaged combination of components such as a substrate and a color development reagent necessary for a method for analyzing a neoepitope.

EXAMPLES

In the following Examples, the present invention is described in detail, but the scope of the present invention is not limited thereto.

[Example 1] Production of Antibodies

For production of antibodies, an application for approval of the animal experiment plan was filed with the Animal Experiment Committee, Shimane University, and the experiment was implemented after obtaining approval.

A peptide (SEQ ID NO: 1, YFGKLESKC) in which cysteine (C) was added to the C-terminus of the peptide at positions 37 to 44 located at the N-terminal sequence of activated IL-18 protein was synthesized according to a conventional method.

Keyhole-limpet hemocyanin (hereinafter referred to as KLH) was crosslinked to the peptide of SEQ ID NO: 1 as a sensitizing antigen using Imject Maleimide-Activated mcKLH spin kit (Thermo Scientific), and then mice were immunized with the obtained peptide according to a conventional method.

The same peptide was crosslinked to bovine serum albumin (hereinafter referred to as BSA) using Imject Maleimide-Activated BSA spin kit (Thermo Scientific), then a screening was performed by ELISA with the obtained peptide. Hybridomas 9-10.2 and 8-4.1 were selected and established. The antibodies produced by hybridomas 9-10.2 and 8-4.1 are referred to as antibody 9-10.2 and antibody 8-4.1, respectively.

Isotypes of monoclonal antibodies 9-10.2 and 8-4.1, which recognize activated IL-18 produced by the hybridomas 9-10.2 and 8-4.1, were confirmed using IsoStrip mouse monoclonal antibody isotyping kit (Sigma), and it was found that they are both IgG1, κ.

[Example 2] Evaluation of Antibodies 9-10.2 and 8-4.1 (By Capillary Western Immunoassay)

Antibodies 9-10.2 and 8-4.1 were compared for their performance with anti-IL-18 antibody having different recognition site (11-4.1, epitope: region at positions 63 to 68 of IL-18, SEQ ID NO: 2, RPLFED). The antibody 11-4.1 is a monoclonal antibody produced by a hybridoma established by the present inventors and has already been shown to detect IL-18 with high sensitivity.

Purified full-length IL-18 expressed in E. coli was mixed with purified active caspase-4$^{19-377}$ which was expressed in E. coli (which means a peptide at positions 105 to 377 of caspase-4. Hereinafter, the peptide may be specified and described with the amino acid positions at the N-terminus and the C-terminus). Thereby activated IL-18 protein (IL-18% 7193) was obtained and purified. The N-terminal sequence of the purified protein was determined by the Edman degradation and found to be YFGKL (SEQ ID NO:42) as expected. This corresponds to tyrosine at position 37, which is the N-terminus of activated IL-18, to leucine at position 41.

Also, an IL-18 protein (positions 37 to 193, having epitope sequence SEQ ID: 4 at N-terminus) with additions of a start codon ATG and a His tag at the C-terminus was expressed in E. coli and purified. In this case, it is considered that, since the next amino acid to initiation methionine (Met) is tyrosine (37Y), methionine aminopeptidase cannot act (Non Patent Literatures 3, 4), thus the initiation methionine does not leave and Met-IL-18$^{37-193}$-His protein is obtained. When the purified protein was subjected to a determination of the N-terminal sequence by Edman degradation, the addition of initiation methionine was found as expected.

Using these proteins, antibodies 9-10.2 and 8-4.1 were compared to the anti-IL-18 antibody having different recognition site (11-4.1, $^{63}$RPLFED$^{68}$ epitope; SEQ ID NO: 2 of IL-18).

Detection of activated IL-18 protein cleaved with activated caspase-4$^{105-377}$ at concentration of 200, 100, 50, and 25 ng/ml and detection of Met-IL-18$^{37-193}$-His protein (the N-terminus of the peptide at position 37 to 193 of the IL-18 protein has epitope SEQ ID: 4) with initiation methionine added to the N-terminus at concentrations of 200 and 100 ng/ml were performed by capillary western immunoassay method using Wes (ProteinSimple). As the primary antibody, each purified antibody was used after adjusted to 0.4 mg/mL and diluted to 125-fold. All other conditions including the secondary antibody and exposure time were the same. The results are shown in FIG. 1.

Although antibodies 9-10.2 and 8-4.1 recognized activated IL-18 protein IL-18$^{37-193}$, they did not recognize Met-IL-18$^{37-193}$-His protein in which methionine was added to the N-terminus of activated IL-18. Meanwhile, antibody 11-4.1 whose epitope is positions 63 to 68 of IL-18 recognized both activated IL-18 (IL-18$^{37-193}$) and Met-IL-18$^{37-193}$-His protein in the same way.

Activated IL-18 and Met-IL-18$^{37-193}$-His protein both contain a region at positions 37 to 193 of IL-18. However, antibodies 9-10.2 and 8-4.1 did not recognize Met-IL-18$^{37-193}$-His protein. That is, these antibodies cannot recognize a peptide in which an amino acid is added to the N-terminus side of tyrosine at position 37, indicating that they recognize IL-18$^{37-193}$ protein, i.e., the neoepitope present in activated IL-18.

[Example 3] Evaluation of Antibodies 9-10.2 and 8-4.1 with Clinical Specimens (Capillary Western Immunoassay Method)

Figure 2:
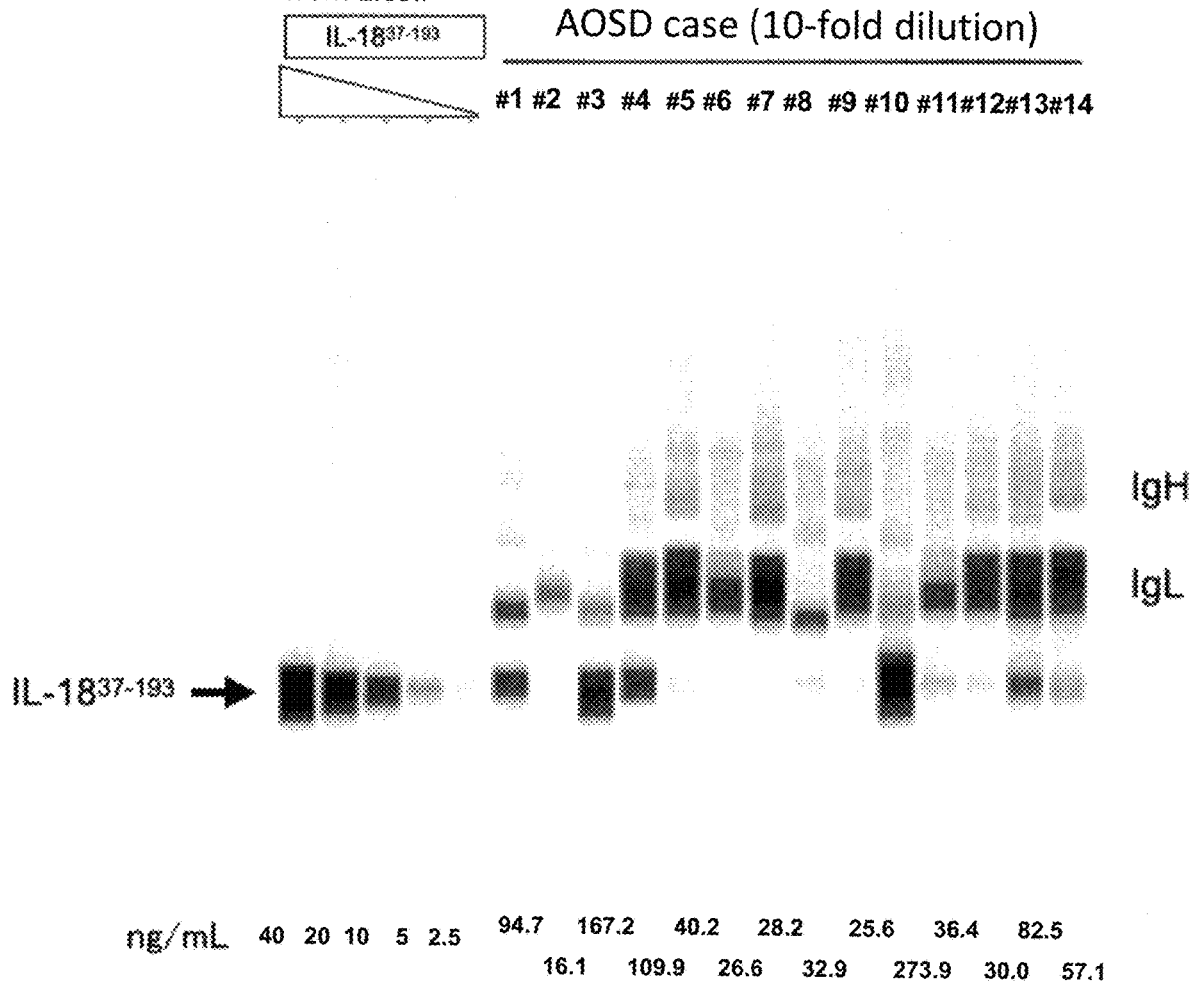
FIG. 2 is a diagram showing the detection results of activated IL-18 in serum of patients with adult onset Still's disease (AOSD).

Adult onset Still's disease (AOSD) is a disease which is reported that IL-18 protein is shown at high levels (Non Patent Literature 5). With approval of the Ethics Committee of the Faculty of Medicine, Shimane University, IL-18 protein in patient serum was detected by capillary western immunoassay method. The patient serum was diluted 10-fold, and the antibody 9-10.2 was used as the primary antibody after adjusted to 0.4 mg/mL and diluted 1:125-fold. The amount and the molecular weight of activated IL-18 contained in the patient serum were analyzed in the same manner as in Example 2, where activated IL-18 protein (IL-18$^{37-193}$) used in Example 2 was used as the standard protein. The results are shown in FIG. 2. In ten patients, the band was detected in the same size as activated IL-18, i.e., IL-18$^{37-193}$ used as the standard protein. As shown in lower part of FIG. 2 as the amount of activated IL-18 present in the patient serum, it was also possible to quantify a very small amount of activated IL-18.

As shown in Example 3, the antibodies 9-10.2 and 8-4.1, which recognize activated IL-18, can be used to detect activated IL-18 by a very simple method.

[Example 4] Application of Antibodies 9-10.2 and 8-4.1 to Immunoprecipitation Method The usefulness of antibodies 9-10.2 and 8-4.1 in immunoprecipitation method was evaluated in comparison to the recognition site-different antibody 11-4.1. IL-18 protein in full-length was expressed in 293T cells with active caspase-4$^{105-377}$. A ready-made Flag-tagged antibody (M2) was used as a negative control antibody. The immunoprecipitation products were detected by western blotting method with a self-made anti-IL-18 rabbit polyclonal antibody. The results are shown in FIG. 3.

Figure 3:
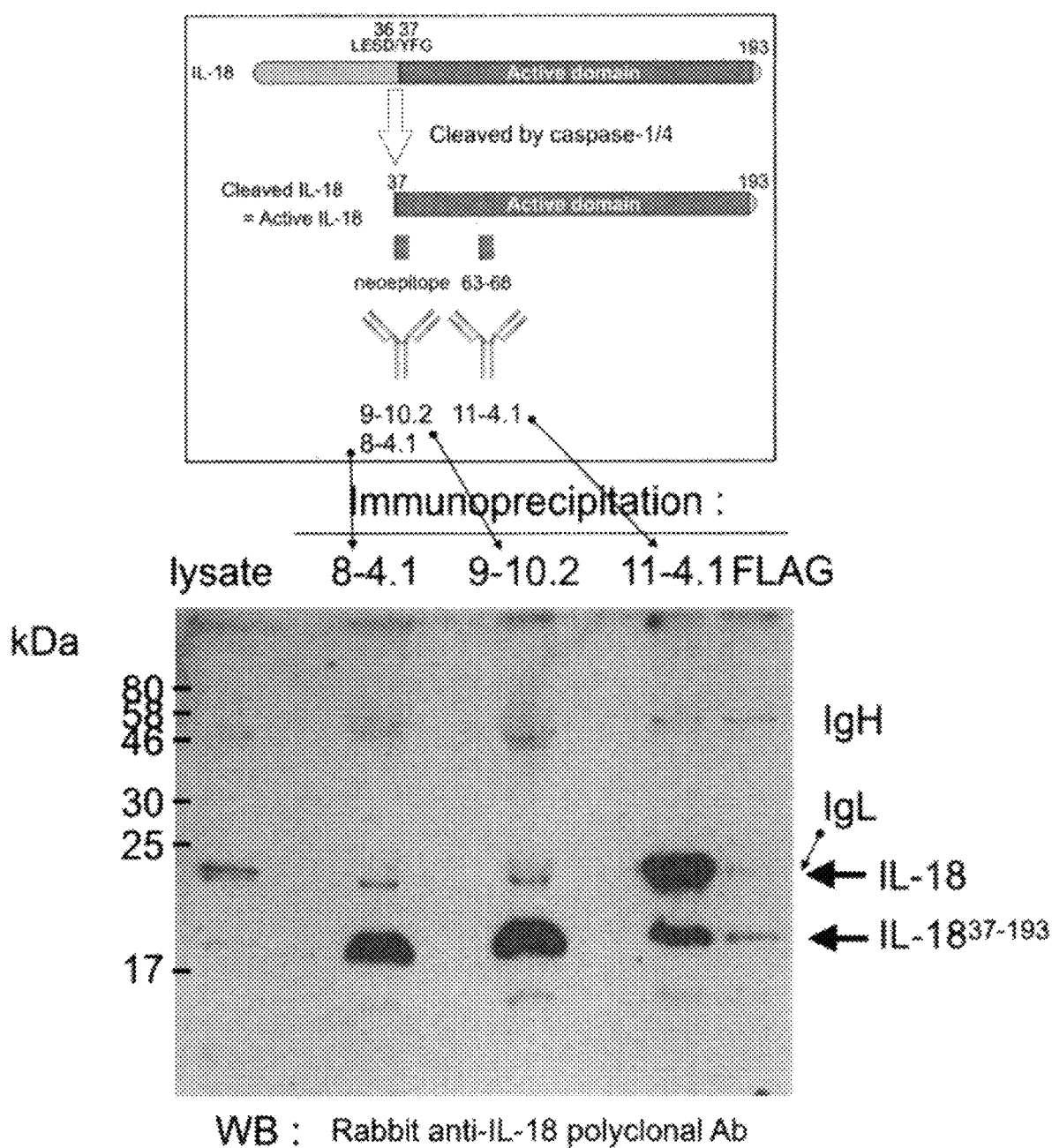
FIG. 3 is a diagram showing the results of application to immunoprecipitation method.

The upper section of FIG. 3 schematically shows full-length IL-18, activated IL-18, and the sites recognized by each antibody. When full-length IL-18 and active caspase-4 are expressed in 293 T cells, full-length IL-18 protein is cleaved by active caspase-4, but uncleaved full-length IL-18 is still present in the cells. The result of immunoprecipitation with antibody 11-4.1 showed a lot of full-length IL-18 protein immunoprecipitated, indicating that a lot of uncleaved pro-IL-18 is present in the cells. Meanwhile, when immunoprecipitation was performed with antibodies 8-4.1 or 9-10.2, full-length IL-18 was not immunoprecipitated, and more IL-18$^{37-193}$ was immunoprecipitated. That is, it has been revealed that antibodies 9-10.2 and 8-4.1 are monoclonal antibodies that can specifically recognize and efficiently immunoprecipitate active IL-18$^{37-193}$ protein cleaved by caspase-4$^{105-377}$ in cells.

[Example 5] Inhibitory Activity of Antibodies 9-10.2 and 8-4.1 to Human IL-18 Function It is known that addition of purified active IL-18 protein expressed in E. coli to acute myeloid leukemia cell line KG-1 (JCRB0065) causes production of IFN-γ (Non Patent Literature 6). If the antibody is an IL-18 function-inhibitory antibody, it inhibits IFN-γ production by IL-18 (see the schematic diagram in upper part of FIG. 4).

Figure 4:
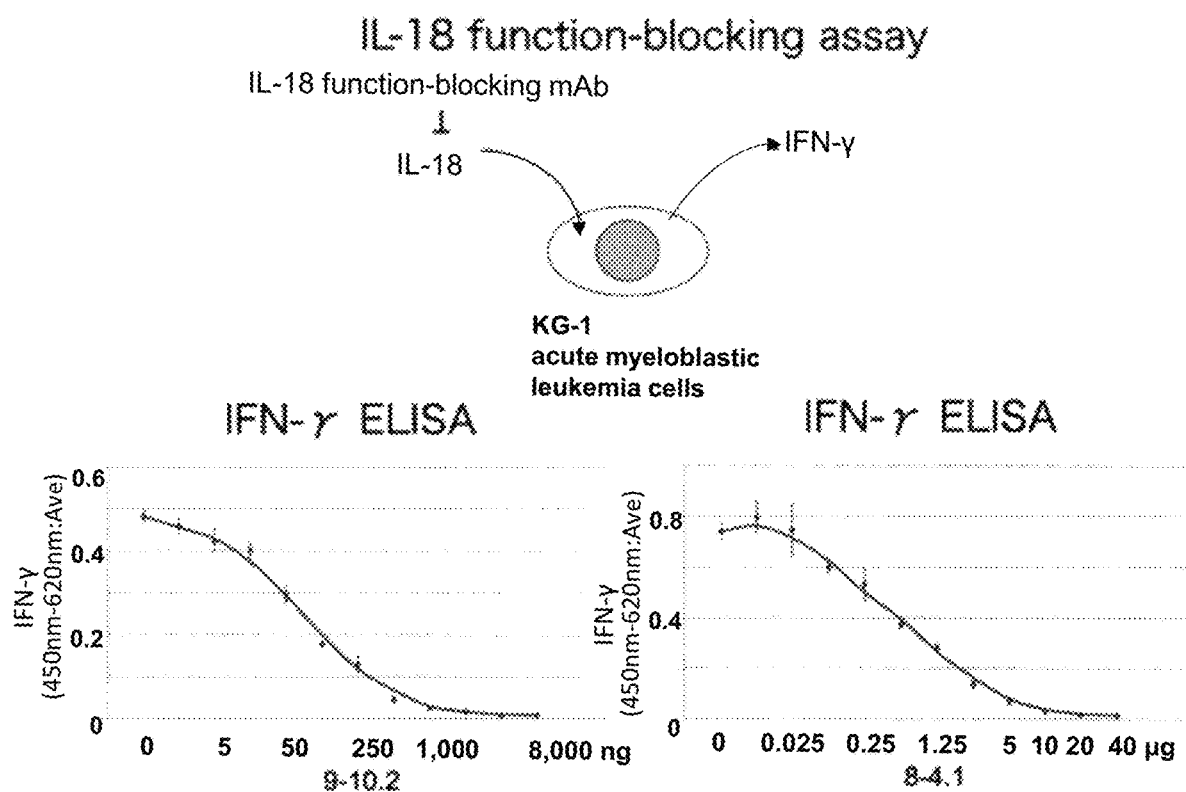
FIG. 4 is a diagram showing inhibitory activity of monoclonal antibodies 9-10.2 and 8-4.1 to human IL-18 function.

To KG-1 cells, 0.5 ng of activated IL-18 and varying concentrations of antibodies 9-10.2 or 8-4.1 were added, and the production of IFN-γ was detected by IFN-γ detection ELISA (Diaclone, Inc., IFN-γ ELISA set). As a result, antibodies 9-10.2 and 8-4.1 exhibited inhibitory activity against production of IFN-γ in an amount-dependent manner (FIG. 4, lower part). Since antibodies 9-10.2 and 8-4.1 both act as an antibody that inhibits human IL-18 function, they can be used to treat diseases caused or exacerbated by overexpression of IL-18. In particular, 9-10.2 showed a very strong inhibitory activity with $IC_H$ of 2.8 nM.

[Example 6] Application of Antibodies 9-10.2 and 8-4.1 to Immunocytostaining Method Full-length IL-18 protein (human IL-18) was expressed in 293T cells in the presence of active caspase-4$^{105-377}$ (G196-

Figure 5:
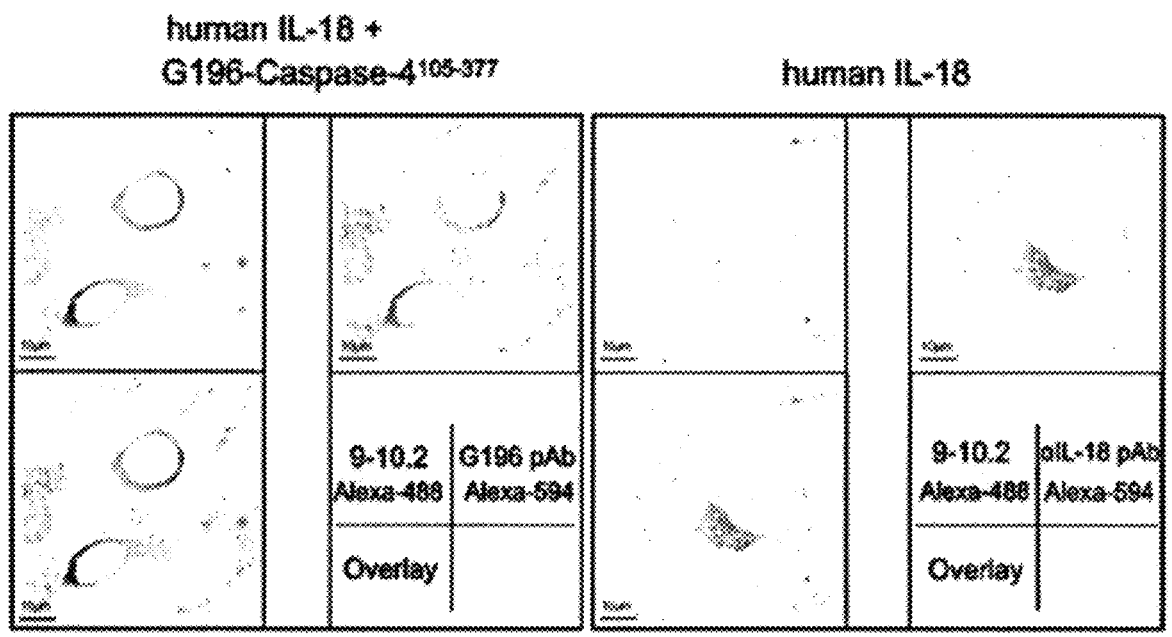
FIG. 5 is a diagram showing application to cell immunostaining method.
Figure 6A:
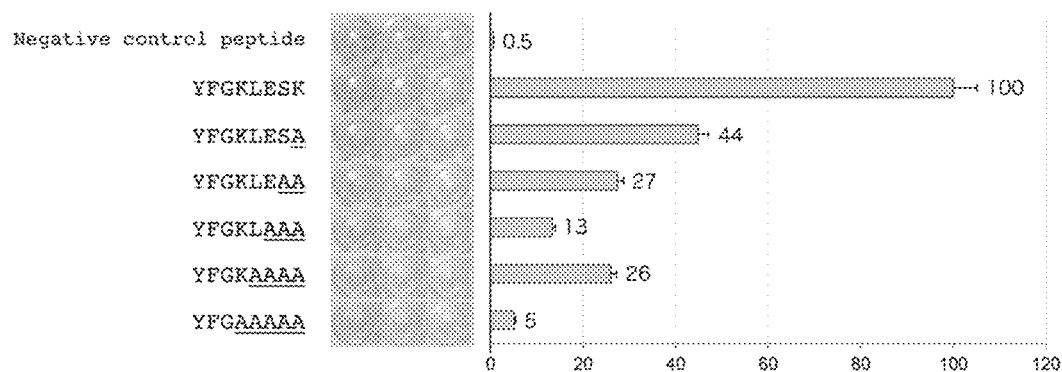
FIG. 6A is a diagram showing the results of epitope analysis by neoepitope fine analysis method of the epitopes of monoclonal antibodies 9-10.2 and 8-4.1.
Figure 6A:
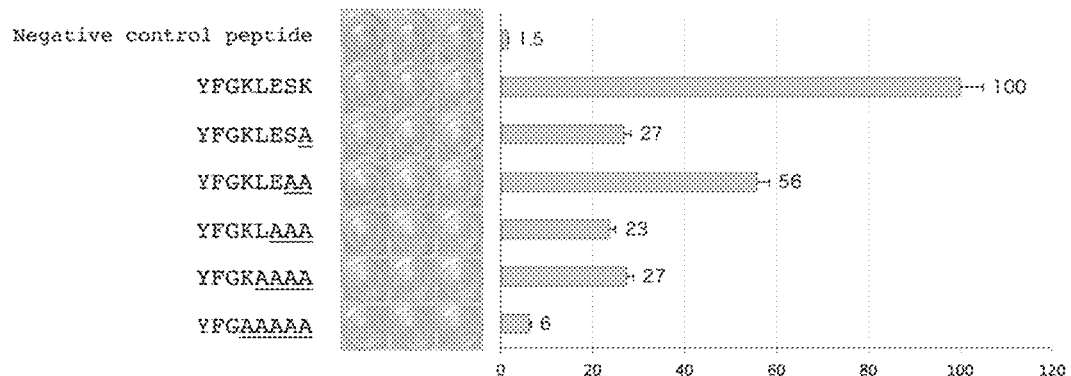
Figure 6B:
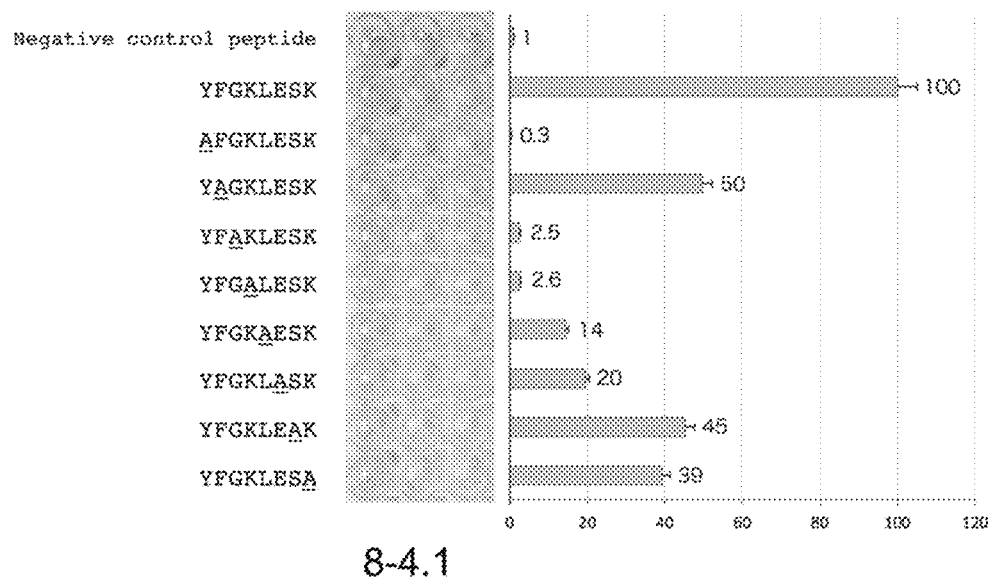
FIG. 6B is a diagram showing the results of epitope analysis by alanine scanning.
Figure 6B:
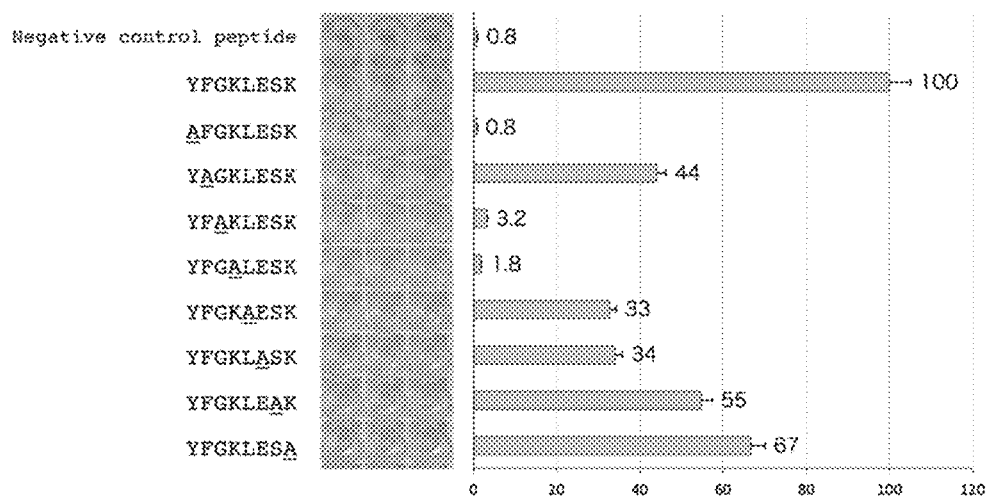

Caspase-4$^{105-377}$) fused with G196 tag (DLVPR, SEQ ID NO: 3, Patent Literature 11) (FIG. 5, left) or in the absence thereof (FIG. 5, right). After immobilization with formalin, the protein was subjected to immunocytostaining with antibody 9-10.2 according to a conventional method.

The presence of active caspase-4$^{105-377}$ was detected by a rabbit polyclonal antibody that recognizes G196 (G196 pAb) (FIG. 5, left, upper right). The presence of IL-18 in the absence of active caspase-4 was detected by a rabbit polyclonal antibody that recognizes IL-18 (aIL-18 pAb) (FIG. 5, right, upper right). In the presence of active caspase-4 (FIG. 5, left), the presence of IL-18 was confirmed by antibody 9-10.2. Meanwhile, in the absence of caspase-4 (FIG. 5, right), despite the presence of IL-18 confirmed by the rabbit polyclonal antibody, IL-18 was not detected by antibody 9-10.2. That is, it indicates that antibody 9-10.2 is a monoclonal antibody that can specifically recognize active IL-18$^{37-193}$ protein cleaved by caspase-4$^{105-377}$ in cells when used also in immunocytostaining method.

[Example 7] Investigation of Epitopes of Antibodies 9-10.2 and 8-4.1

When a protein is cleaved by a proteolytic enzyme such as a caspase as described above, a neoepitope that is a protein cleaved end not present in the original protein is formed. In the neoepitope peptide used for antibody production, peptides were substituted by sequentially and successively with alanine from the amino acid at the N-terminus or C-terminus opposite to the neoepitope cleaved end important for antibody recognition; and the region of neoepitope recognized by the antibody was identified. This method of determining a region of a neoepitope recognized by an antibody was named "neoepitope fine analysis method". The neoepitope fine analysis method is a method of determining an epitope of an antibody by successively substituting with alanine, unlike an alanine scanning method in which one amino acid is substituted with alanine at a time. The neoepitope fine analysis method is an excellent method for determining a binding region of an antibody in a neoepitope. Although quantitative analysis was performed by ELISA as shown below, the analysis can also be performed by SPR method or the like, not limited to ELISA. In addition, although analysis was performed by substituting with alanine in the Examples below, the analysis can also be performed with an amino acid having a small molecular weight and not causing a major structural change, such as glycine.

Neoepitope peptides (positions 37 to 44, SEQ ID: NO. 4) substituted with alanine by sequentially and successively starting from lysine at position 44 (K44) at the C-terminus and Cys for crosslinking was added to the C-terminus were synthesized according to a conventional method. To each peptide, BSA was crosslinked with Imject Maleimide-Activated BSA spin Kit, and the recognition sites of the antibodies 9-10.2 and 8-4.1 were analyzed by ELISA. In the right of the ELISA plate photograph in FIG. 6 (A), the absorbance obtained with a plate reader was shown along with the standard deviation with setting the wild-type peptide as 100.

Both antibodies exhibit little reactivity to the peptides in which lysine at positions 40 to 44 are substituted with alanine, but exhibit to the peptides having the presence of lysine at position 40 at reactivity of about ¼ of the wild-type peptide. In addition, a decrease in the number of alanine substituting from positions 41 to 43 does almost not alter the reactivity of the antibody.

Next, epitope analysis was performed by alanine scanning method. The peptide of the N-terminal sequence (positions 37 to 44) of activated IL-18 protein added cysteine for crosslinking at the C-terminus (YFGKLESKC, SEQ ID NO: 1), alanine variants of each amino acid in the peptide were synthesized according to a conventional method. In the same way as described above, recognition site analysis of antibodies 9-10.2 and 8-4.1 was performed by ELISA with each peptide crosslinked by BSA (FIG. 6(B)).

Both antibodies 9-10.2 and 8-4.1 were almost unable to recognize the peptide (Y37A) in which the first amino acid (tyrosine (Y) at position 37) of the N-terminal sequence of activated IL-18 protein was replaced with alanine (A), and peptide G39A and peptide K40A were also not recognized. Furthermore, antibodies 9-10.2 and 8-4.1 showed weak binding to the variants of L41A, and E42A, and approximately 50% binding to the variants of F38A, S43A, and K44A.

Figure 7A:
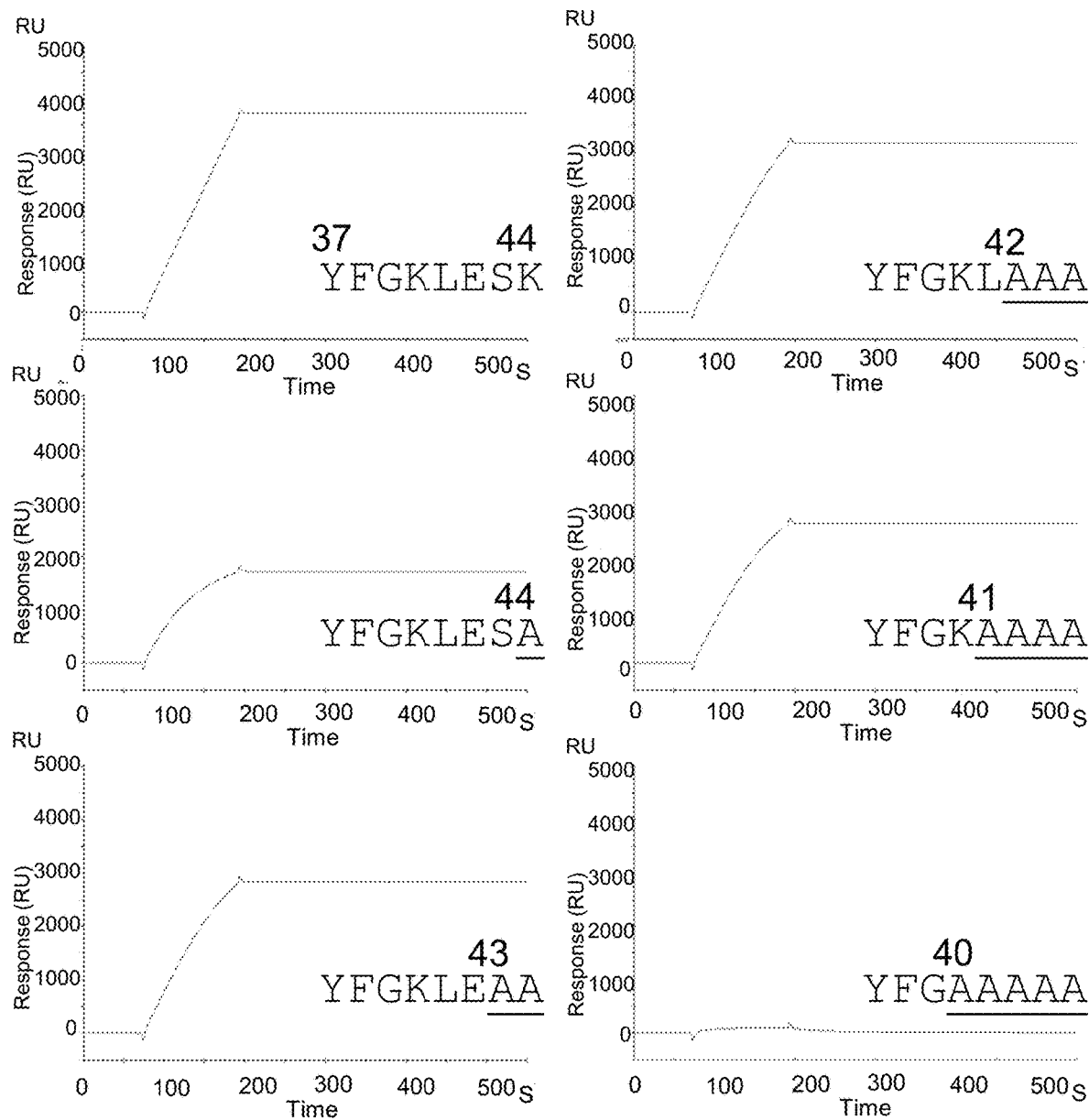
FIG. 7A shows a sensorgram of surface plasmon resonance analysis by neoepitope fine analysis method for monoclonal antibody 9-10.2 with IL-18$^{37-44}$ peptide.

Surface plasmon resonance analysis was further performed using the same peptides. Neoepitope peptides (positions 37 to 44) substituted with alanine sequentially and successively from lysine at position 44 (K44) at the C-terminus and added Cys for crosslinking to the C-terminus were each immobilized to sensor chip CM5 (GE Healthcare, BR100012) by ligand thiol coupling method. Purified antibody 9-10.2 was subjected to "neoepitope fine analysis" at a concentration of 50 nM by measuring with Biacore X100 (GE Healthcare) by single-cycle (FIG. 7(A)).

The antibody did not bind at all to the peptides in which lysine at positions 40 to 44 were substituted with alanine, but showed binding to the peptide having the presence of lysine at position 40. In addition, with the presence of lysine at position 40, a decrease in the number of alanine substituting from positions 41 to 43 did almost not alter the reactivity of the antibody for dissociation from the peptide.

Figure 7B:
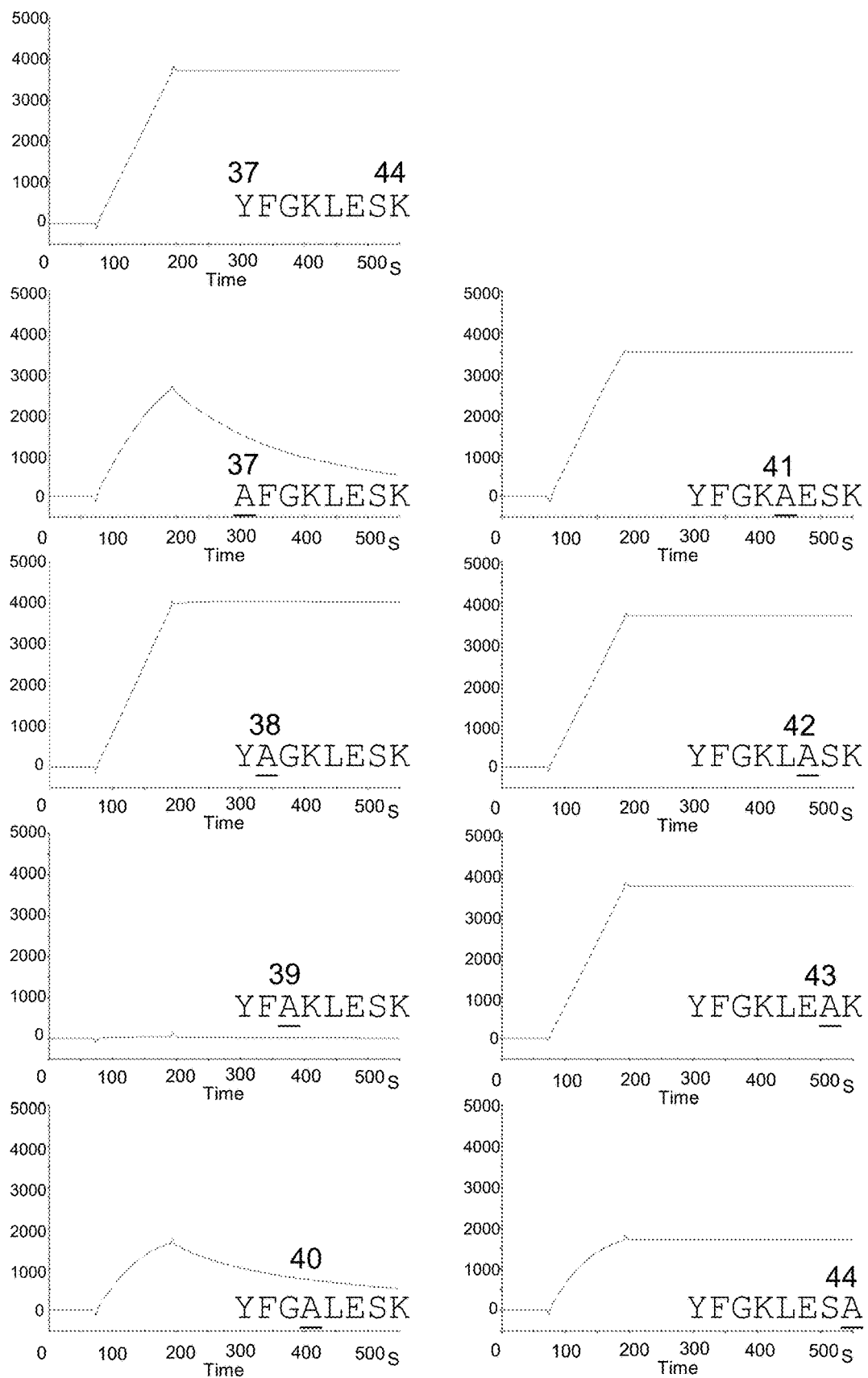
FIG. 7B shows a sensorgram of surface plasmon resonance analysis by alanine scanning.

Next, alanine variants of each amino acid in a peptide (YFGKLESKC, SEQ ID NO: 1), where cysteine for crosslinking was added to the C-terminus of the N-terminal sequence (positions 37 to 44) of activated IL-18 protein, were immobilized to sensor chip CM5 by ligand thiol coupling method. Purified antibody 9-10.2 was subjected to "alanine scanning analysis" at a concentration of 50 nM by measuring with Biacore X100 by single-cycle (FIG. 7(B)).

The antibody 9-10.2 was unable to recognize the peptide (G39A) in which the third amino acid (glycine (G) at position 39) of the N-terminal sequence of activated IL-18 protein was replaced with alanine (A). It has been found that antibody 9-10.2 easily dissociates from Y37A and K40A variants, and has no changes of dissociation for the variants of F38A, L41A, E42A, S43A and K44A.

The same result was obtained in surface plasmon resonance analysis as that in analysis by ELISA shown in FIG. 6. Core regions important for binding can be obtained by "neoepitope fine analysis", and information on amino acids important for binding can be obtained by "alanine scanning analysis".

Figure 7C:
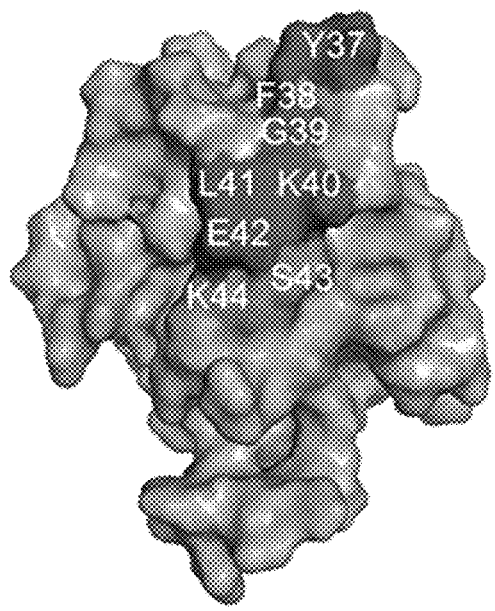
FIG. 7C is a diagram showing the position of the epitope on a three-dimensional structure.
Figure 8:
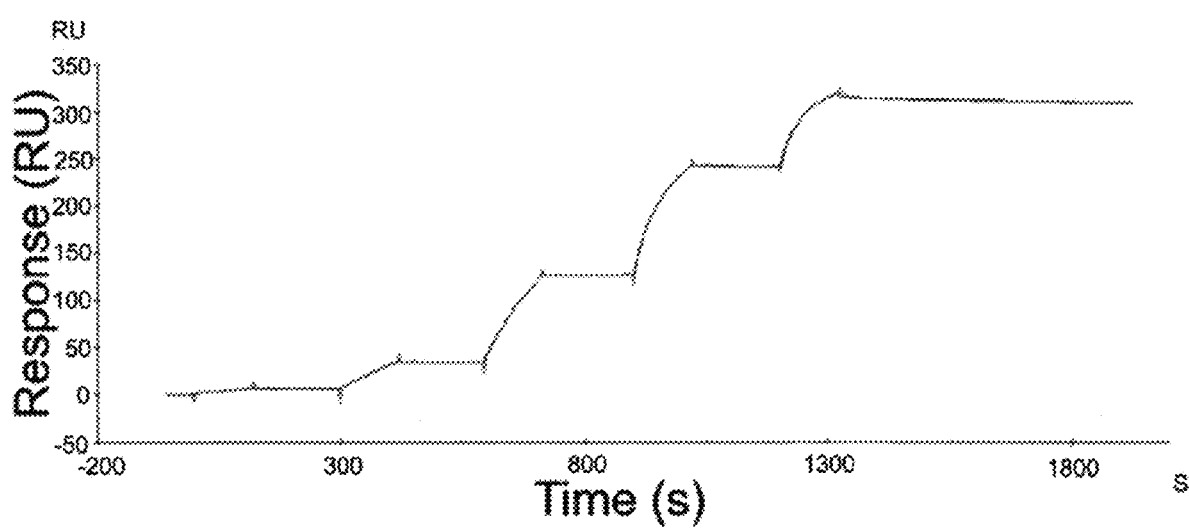
FIG. 8 shows a sensorgram of surface plasmon resonance analysis for antibody 9-10.2 with IL-18$^{37-44}$ peptide.
Figure 9:
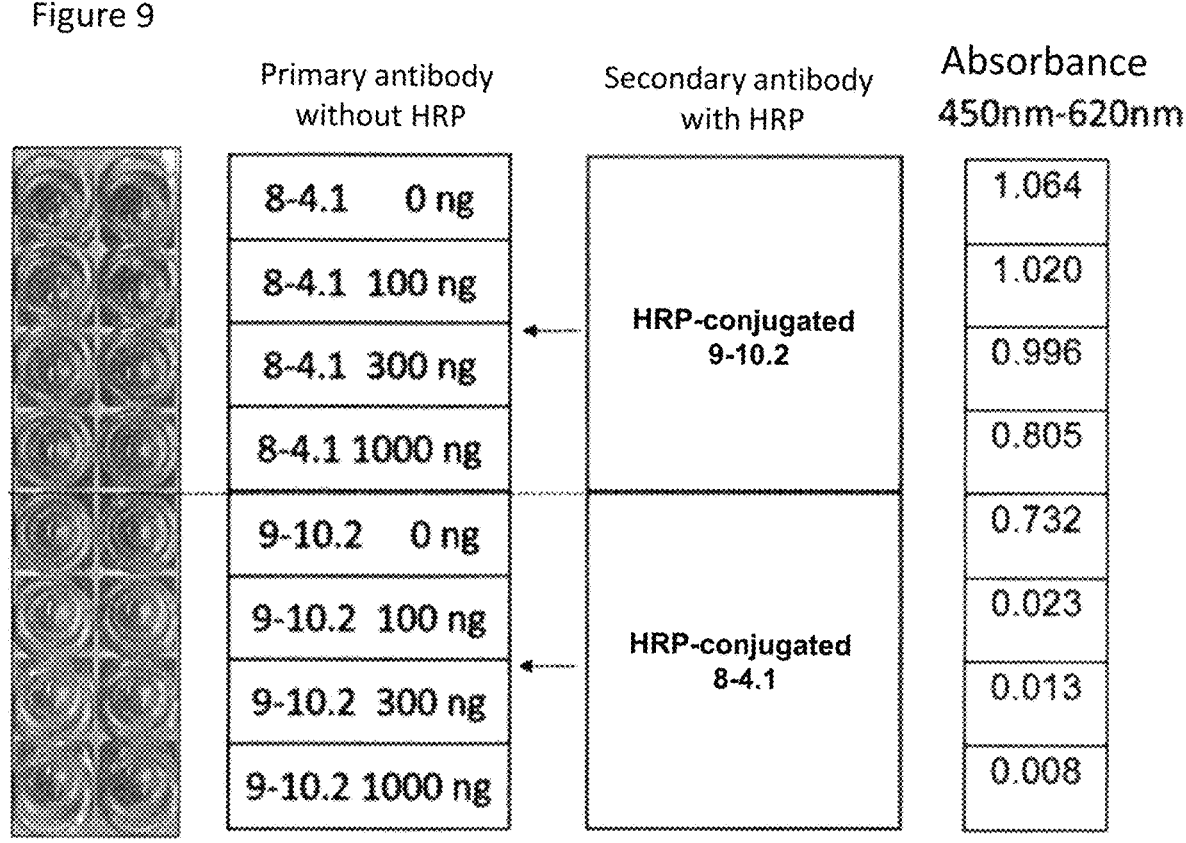
FIG. 9 is a diagram showing the results of a competition experiment of monoclonal antibodies 9-10.2 and 8-4.1.

Considering together with known NMR structural analysis of human IL-18 (PDB: 1JOS, FIG. 7(C)), it is believed that 8 amino acids from tyrosine at position 37 (Y37) to lysine at position 44 (K44) exposed to the structural surface are important for recognition by antibodies 9-10.2 and 8-4.1.

Furthermore, from the results of the above neoepitope fine analysis method, it has been revealed that peptides from positions 37 to 40 are particularly important for the recognition by antibodies 9-10.2 and 8-4.1. In other words, it has been revealed that both antibodies 9-10.2 and 8-4.1 recognize YFGKLESK (SEQ ID NO: 4) as epitope and YFGK (SEQ ID NO: 5) as minimal epitope.

The peptide YFGKLESK (SEQ ID NO: 4) or YFGK (SEQ ID NO: 5) is an epitope to which an antibody that recognizes activated IL-18 binds. Thus, there are possibilities that they can be used as a vaccine containing a peptide having the sequence as an immunogen, or as a therapeutic agent including a region containing this peptide and a peptide of another IL-18 region that binds to an IL-18 receptor in combination.

Among IL-18BPs, binding sites of IL-18 to 3F62 (IL-18BP of poxvirus) and 4EEE (IL-18BP of yatapovirus) are structurally analyzed and contain the regions of Y37, F38, and G39 (these amino acids are present in SEQ ID: NO. 4), Non Patent Literatures 7 and 8). Although structural analysis of human IL18BP has not yet been performed, they are similar in the primary sequence, thus human IL18BP is likely to bind to the same region. It is believed that antibodies 9-10.2 and 8-4.1 do not bind to IL-18 bound by IL-18BP. Thus, by using these antibodies, it is possible to measure IL-18 free of bound by IL-18BP.

Specifically, antibodies 9-10.2 or 8-4.1 are coated onto a substrate and reacted with serum. Antibodies 9-10.2 and 8-4.1 cannot bind to IL-18 bound by IL-18BP, and only capture activated IL-18 in which the neoepitope is exposed. The captured IL-18 may be reacted with an antibody that recognizes another site to be measured. Thus, it is also possible to easily measure IL-18 free of bound by IL-18BP, which was previously measured in a cumbersome manner by ELISA.

[Example 8] Affinity Analysis Between Antibody 9-10.2 and IL-$18^{37-44}$ Peptide (Surface Plasmon Resonance Analysis)

The peptide (YFGKLESKC, SEQ ID NO: 1) in which cysteine for crosslinking was added to the C-terminus of the neoepitope peptide (positions 37 to 44) of activated IL-18 protein was immobilized to sensor chip CM5 by ligand thiol coupling method. Purified antibody 9-10.2 was used at 5 concentrations in the range of 0.4 nM to 250 nM with a series of 5-fold dilution to measure with Biacore X100 by single-cycle (FIG. 8). The analysis was performed by bivalent analysis.

The results were $K_D$: $1.9\times10^{-10}$ M, $K_a$: $2.1\times10^{5}$ $M^{-1}s^{-1}$, and $K_d$: $4.0\times10^{-3}$ $s^{-1}$. It has been revealed that antibody 9-10.2 binds to the N-terminal sequence peptide of activated IL-18 protein with very high affinity.

[Example 9] Competitive Experimental Analysis of Monoclonal Antibodies 9-10.2 and 8-4.1

From the epitope analysis of Example 7, it is believed that monoclonal antibodies 9-10.2 and 8-4.1 recognize the same epitope. Furthermore, from the results of Example 8, it was revealed that antibody 9-10.2 binds to the neoepitope with very high affinity. Thus, competitive experiments between monoclonal antibodies 9-10.2 and 8-4.1 were performed, and to analyze whether antibodies 9-10.2 and 8-4.1 recognize the same epitope (FIG. 9).

The peptide of SEQ ID NO: 1 (YFGKLESKC) was crosslinked to BSA, adjusted to 5 ng/100 μl with 50 mM $NaHCO_3$, and coated on an ELISA plate overnight at 4° C. The ELISA plate was blocked and washed by a conventional method, and an antibody solution of 9-10.2 or 8-4.1 adjusted to 0, 100, 300, or 1000 ng/100 μl was added, and the reaction was carried out at 25° C. for 1 hour. The wells without antibody were only added with a wash solution (see FIG. 9, primary antibody without addition of HRP).

Next, each antibody labeled with HRP (0.5 μg/μ1) was diluted 100-fold with the wash solution. Then, antibody 9-10.2 labeled with HRP was added at 100 μl to the wells in which antibody 8-4.1 was bound to the peptide as the primary antibody, and the antibody 8-4.1 labeled with HRP was added at 100 μl to the wells in which antibody 9-10.2 was bound to the peptide, and then the wells were incubated at 25° C. for 1 hour (see FIG. 9, secondary antibody with addition of HRP). Afterwards, the wells were washed, color was developed, and absorbance was measured (see FIG. 9, absorbance 450 nm to 620 nm).

It has been shown that, when antibody 8-4.1 is used as the primary antibody, and antibody 9-10.2 labeled with HRP is used as the secondary antibody, antibody 9-10.2 binds to the peptide as the result of competition with antibody 8-4.1 that is the primary antibody. Accordingly, it has been revealed that antibodies 9-10.2 and 8-4.1 compete with each other and antibody 9-10.2 has high affinity to activated IL-18 compared to antibody 8-4.1.

[Example 10] Gene Analysis of Antibody

Next, gene analysis of each antibody was performed. RNA was extracted from hybridomas 9-10.2 and 8-4.1, and then reverse-transcribed with an oligo-dT primer to generate cDNA. The synthesized cDNA was used to determine the sequence of the hypervariable region of the antibody gene and the amino acid sequence by direct sequencing using a primer set of H and L chains.

The primer sequences of the H and L chains used are as follows.

```
H-chain primer
VH1-1S:
                                   (SEQ ID NO: 6)
5'-ggggatcc ag gts mar ctg cag sag tcw gg-3'
s = g + c, m = a + c, r = a + g, w = a + t IgG2-1AS:
                                   (SEQ ID NO: 7)
5'-gggaattc ctt gac cag gca tcc tag agt ca-3'

L-chain primer
VK-1S:
                                   (SEQ ID NO: 8)
5'-ggggatcc gay att gtg mts acm car wct mca-3
y = c + t, m = a + c, s = g + c, r = a + g,
w = a + t CK-2AS:
                                   (SEQ ID NO: 9)
5'-gggaattc gaa gat gga tac agt tgg tgc-3'
```

Note that the underlines indicate recognition sites of restriction enzymes.

By gene analysis of the H chain, the nucleotide sequence (SEQ ID NO: 10) and the amino acid sequence (SEQ ID NO: 11) of the H chain of antibody 9-10.2, and the nucleotide sequence (SEQ ID NO: 12) and the amino acid sequence (SEQ ID NO: 13) of the H chain of antibody 8-4.1 were determined. Also, by gene analysis of the L chain, the nucleotide sequence (SEQ ID NO: 14) and the amino acid sequence (SEQ ID NO: 15) of the L chain of antibody 9-10.2, and the nucleotide sequence (SEQ ID NO: 16) and the amino acid sequence (SEQ ID NO: 17) of the L chain of antibody 8-4.1 were determined.

The amino acid sequences and the nucleotide sequences of complementarity determining regions (CDRs) of antibodies 9-10.2 and 8-4.1 are summarized below.

TABLE 1

Nucleotide Sequence of 9-10.2 Antibody

| | Heavy Chain | SEQ ID | | Light Chain | SEQ ID |
|---|---|---|---|---|---|
| CDRH1 | GGGTTTTCACTGAGCAGTTCTGGTATGGGT | 18 | CDRL1 | CAGAGCATTGCACATAGTAATGGATACACTAT | 21 |
| CDRH2 | ATTTGGTGGGATGATGATAAG | 19 | CDRL2 | AAAGTTTCC | 22 |
| CDRH3 | ACTCGAACGAGGACGTATAGTAACTTCGGAGGTGGTATGGCCTAC | 20 | CDRL3 | GTTCAAGGTTCACATGTTCCGCTCACG | 23 |

TABLE 2

Amino Acid Sequence of 9-10.2 Antibody

| | Heavy Chain | SEQ ID | | Light Chain | SEQ ID |
|---|---|---|---|---|---|
| CDRH1 | GFSLSSSGMG | 24 | CDRL1 | QSIAHSNGYTY | 27 |
| CDRH2 | IWWDDDK | 25 | CDRL2 | KVS | 28 |
| CDRH3 | TRTRTYSNFGGGMAY | 26 | CDRL3 | VQGSHVPLT | 29 |

TABLE 3

Nucleotide Sequence of 8-4.1 Antibody

| | Heavy Chain | SEQ ID | | Light Chain | SEQ ID |
|---|---|---|---|---|---|
| CDRH1 | GGGTTTTCATTAACCAGCTATGGT | 30 | CDRL1 | GAGAATGTGGTTACTTAT | 33 |
| CDRH2 | ATATGGGCTGGTGGAAGCACA | 31 | CDRL2 | GGGGCATCC | 34 |
| CDRH3 | GCCAGAGAAAGTAGCTACGATGCTATGGACTAC | 32 | CDRL3 | GGACAGGGTTACAGCTATCCGTACACG | 35 |

TABLE 4

Amino Acid Sequence of 8-4.1 Antibody

| | Heavy Chain | SEQ ID | | Light Chain | SEQ ID |
|---|---|---|---|---|---|
| CDRH1 | GFSLTSYG | 36 | CDRL1 | ENVVTY | 39 |
| CDRH2 | IWAGGST | 37 | CDRL2 | GAS | 40 |
| CDRH3 | ARESSYDAMDY | 38 | CDRL3 | GQGYSYPYT | 41 |

As shown in the Examples, the antibody having the above CDR is an antibody that specifically recognizes activated IL-18 with high sensitivity and specificity. Thus, it enables to detect activated IL-18 by a method that can be easily carried out in clinical sites, such as ELISA. As a result, it is possible to easily determine in the clinical site whether it is an IL-18-related disease or not, and the determination can be used to formulate a treatment strategy. In addition, since the antibody can be applied to various methods such as western blotting, capillary western immunoassay, immunoprecipitation, and immunocytostaining, it can also be widely used as a research reagent. Furthermore, since it has been revealed that the function of IL-18 can be inhibited, the antibody is also very useful as an agent for treating an IL-18-related disease.

The invention claimed is:

1. An anti-IL-18 monoclonal antibody comprising: a heavy chain variable region, wherein the heavy chain variable region comprises:
   a CDR1H region consisting of the amino acid sequence of SEQ ID NO: 24,
   a CDR2H region consisting of the amino acid sequence of SEQ ID NO: 25, and
   a CDR3H region consisting of the amino acid sequence of SEQ ID NO: 26; and
   a light chain variable region, wherein the light chain variable region comprises:
   a CDR1L region consisting of the amino acid sequence of SEQ ID NO: 27,
   a CDR2L region consisting of the amino acid sequence of SEQ ID NO: 28, and
   a CDR3L region consisting of the amino acid sequence of SEQ ID NO: 29.

2. The anti-IL-18 antibody according to claim 1, wherein an amino acid sequence of the heavy chain variable region is SEQ ID NO: 11 and an amino acid sequence of the light chain variable region is SEQ ID NO: 15.

3. A nucleic acid encoding, as an open reading frame, from a heavy chain variable region and a light chain variable region,
   wherein the heavy chain variable region comprises:
   a CDR1H region consisting of the amino acid sequence of SEQ ID NO: 24;
   a CDR2H region consisting of the amino acid sequence of SEQ ID NO: 25;
   a CDR3H region consisting of the amino acid sequence of SEQ ID NO: 26,
   the light chain variable region comprises:
   a CDR1L region consisting of the amino acid sequence of SEQ ID NO: 27;
   a CDR2L region consisting of the amino acid sequence of SEQ ID NO: 28; and
   a CDR3L region consisting of the amino acid sequence of SEQ ID NO: 29.

4. A nucleic acid encoding, as an open reading frame, a heavy chain variable region and a light chain variable region, wherein the heavy chain variable region consists of the amino acid sequence of SEQ ID NO: 11, the light chain variable region consists of the amino acid sequence of SEQ ID NO: 15.

5. A functional fragment of the anti-IL-18 monoclonal antibody according to claim 1.

6. A kit for detecting and/or quantifying IL-18 peptide cleaved into 37th to 193rd positions, comprising the anti-IL-18 monoclonal antibody according to claim 1.

7. The anti-IL-18 monoclonal antibody to claim 1, wherein the anti-IL-18 monoclonal antibody is a humanized antibody.

8. A functional fragment of the anti-IL-18 monoclonal antibody according to claim 7.

9. A pharmaceutical composition for use in treating an IL-18-related disease, comprising the anti-IL-18 monoclonal antibody according to claim 7 as an active ingredient.

10. A pharmaceutical composition for use in treating an IL-18-related disease, comprising the functional fragment according to claim 8 as an active ingredient.

* * * * *